(12) United States Patent
Van Den Berghe

(10) Patent No.: US 7,446,091 B2
(45) Date of Patent: Nov. 4, 2008

(54) METHODS AND PREPARATIONS FOR CURING CLINICALLY ILL PATIENTS

(75) Inventor: Greta Van Den Berghe, Nethen-Grez-Doiceau (BE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/853,193

(22) Filed: May 11, 2001

(65) Prior Publication Data
US 2002/0107178 A1    Aug. 8, 2002

Related U.S. Application Data

(63) Continuation of application No. PCT/DK01/00287, filed on Apr. 30, 2001.

(30) Foreign Application Priority Data

| May 5, 2000 | (GB) | ................................. | 0010856.3 |
| Apr. 15, 2001 | (DK) | ............................. | 2001 00604 |
| Apr. 16, 2001 | (DK) | ............................. | 2001 00605 |

(51) Int. Cl.
*A61K 38/28* (2006.01)
(52) U.S. Cl. ................. 514/3; 514/2; 514/12; 530/303; 424/9.1
(58) Field of Classification Search ..................... 514/3, 514/2, 12; 530/303; 424/9.1
See application file for complete search history.

(56) References Cited

U.S. PATENT DOCUMENTS

| 5,000,953 A | 3/1991 | Ui et al. | |
| 5,155,031 A | 10/1992 | Posner et al. | |
| 5,547,929 A * | 8/1996 | Anderson et al. | ............... 514/3 |
| 5,614,492 A | 3/1997 | Habener | |
| 5,618,913 A * | 4/1997 | Brange et al. | ................ 530/303 |
| 5,691,386 A | 11/1997 | Inman et al. | ................. 514/691 |
| 5,750,497 A * | 5/1998 | Havelund et al. | ............... 514/3 |
| 5,821,217 A | 10/1998 | Forse et al. | ..................... 514/2 |
| 5,861,266 A | 1/1999 | Ullrich et al. | |
| 5,885,980 A * | 3/1999 | Gutierrez et al. | ............. 514/186 |
| 6,277,819 B1 | 8/2001 | Efendic | ........................ 514/12 |
| 6,335,316 B1 | 1/2002 | Hughes et al. | |
| RE37,971 E | 1/2003 | Baker et al. | |
| 6,551,992 B1 | 4/2003 | DeFelippis et al. | |

FOREIGN PATENT DOCUMENTS

| WO | WO 95/23217 | 8/1995 |
| WO | 97/07814 | 3/1997 |
| WO | 98/08531 | 3/1998 |
| WO | 98/08873 | 3/1998 |
| WO | WO 00/16797 | 3/2000 |
| WO | 00/33839 | 6/2000 |
| WO | WO 01/85256 | 11/2001 |
| WO | 03/028626 | 4/2003 |

OTHER PUBLICATIONS

Abstract US 19925044940, Novo Blood Cir.Path.Inst. Derwent Accession No. 1996-096010 [10].
K. O. Case et al., "Nutrition Support in the Critically Ill Patient", Crit. Care Nurs Q 2000 vol. 22 No. 4. pp. 75-79 (2000).
Y. Sakuri et al., "Stimulation of Muscle Protein Synthesis By Long-Term Insulin Infusion in Severly Burned Patients", Annals of Surgery, vol. 222, No. 3, pp. 283-297(1995).
K.C. McCowen et al., "Stress-Induced Hyperglycemia", Critical Care Clinics vol. 17, No. 1, pp. 107-124 (2001).
Press Release "Clinical Study demonstrates impressive life-saving Effects of insulin by tight control of glucose in intensive care patients" pp. 1-3 (Nov. 8, 2001).
UK Prosperctive Diabetes Study (UKPDS) Group "Intensive blood-glucose Control with supphonylureas or insulin compared with conventional treatment and risk of complications in patients with type 2 diabetes" The Lancet vol. 352. pp. 837-853 (1998).
Nathan et al., "The Effect of Intensive Treatment of Diabetes on the Development and Progression of Long-Term Complications in Insulin-Dependent Diabetes Mellitus" The New England Journal of Medicine, vol. 329, No. 14. pp. 977-986 (1993).
G. Van Den Berghe et al., "Intensive Insulin Therapy in Critically Ill Patients" The New England Journal of Medicine. vol. 345, No. 19 pp. 1359-1367 (2001).
Zochodne et al "Critical Illness Polyneuropathy-A Complication of Sepsis and Multiple Organ Failure" Brain vol. 110, pp. 819-842 (1987).
Leijten et al, "Critical Illness Polyneuropathy—A review of the literature, definition and pathophysiology" Clinical Nuerology and And Neurosurgery. vol. 96. pp. 10-19 (1994).
C.F. Bolton "7.8 Acute Weakness" 7 The Neurological System, pp. 490-495.
C.F. Bolton, "Sepsis and the systemic inflammatory response syndrome: Neuromuscular manifestations" Crit Care Med. vol. 24, No. 8, pp. 1408-1416 (1996).
R.R.Wolfe et al., "Glucose Metabolism in Man: Responses to Intravenous Glucose Infusion" Metabolism, vol. 28 No. 3. pp. 210-220 (1979).
R. R. Wolfe et al., "Effect of Severe Burn Injury on Substrates Cycling by Glucose and Fatty Acids" The New England Journal of Medicine, vol. 317, No. 7, pp. 403-408 (1987).
R.E.Shangraw et al., "Differentiation Between Septic and Postburn Insulin Resistance", Metabolism, vol. 38, No. 10. pp. 983-989 (1989).

(Continued)

*Primary Examiner*—Chih-Min Kam
(74) *Attorney, Agent, or Firm*—Richard W. Bork

(57) ABSTRACT

This invention relates to a life saving medicament for critically ill patients and a method of treatment. The composition is a pharmaceutically effective amount of a blood glucose regulator which is used to control the blood glucose level.

15 Claims, 2 Drawing Sheets

OTHER PUBLICATIONS

B.A. Mizock et al., "Alterations in Carbohydrate Metabolism During Stress: A Review of the Literature" The American Journal of Medicine, vol. 98, pp. 75-84 (1995).

K.C. McCowen et al., "Stress-Induced Hyperglycemia" Critical care Clinics, vol. 17, No. 1, pp. 107-124 (2001).

R. Fietsman et al., "Complications of Coronary Artery Surgery in Diabetic Patients" The American Surgeon vol. 57, pp. 551-557 (1991).

P.A.O'Neill et al., "Stress Hormone and Blood Glucose Response Following Acute Stroke in the Elderly" Stroke,vol. 22,pp. 42-847 (1991).

J.F. Scott et al., "Glucose Potassium Insulin Infusions in the Treatment of Acute Stroke Patients with Mild to Moderate Hyperglycemia" The Glucose Insulin in Stroke Trial (GIST) Stroke, vol. 30, pp. 793-799 (1999).

K. Malmberg et al., "Glycometabolic State at Admission:Important Risk Marker of Mortality in Conventionally Treated Patients With Diabetes Mellitus and Acute Myocardial Infarction" Circulation vol. 99, pp. 2626-2632 (1999).

K. Malmberg, "Prospective randomized study of intensive insulin treatment on long term survival after acute myocardial infarction in Patients with diabetes mellitus" BMJ, vol. 314:1512, pp. 1-12(1997).

K. Malmberg et al., "Randomized Trial of Insulin-Glucose Infusion Followed by Subcutaneous Insulin Treatment in Diabetic Patients With Acute Myocardial Infarction (GIGAMI Study) :Effects on Mortality at 1 Year" J. Am. Coll Cardio vol. 26, pp. 57-65 (1995).

G. Van Den Berghe et al., "Reactivation of Pituitary Hormone Release and Metabolic Improvement by Infusion of Growth Hormone-Releasing Peptide and Thyrotropin-Releasing Hormone in Patients with Protracted Critical Illness" The Journal of Clinical Endocrinology & Metabolism. vol. 84, No. 4, pp. 1311-1323 (1999).

G. Van Den Berghe et al., "A Paradoxical Gender Dissociation within the Growth Hormone/Insulin-Like Growth Factor I Axis during Protracted Critical Illness" The Journal of Clinical Endocrinology & Metabolism vol. 85. No. 1 pp. 183-192 (2000).

A. Ortiz et al., "Expression of Apoptosis-Regulatory Genes in Renal Proximal Tubular Epithelial Cells Exposed to High Ambient Glucose and In Diabetic Kidneys" Journal of Investigative Medicine vol. 45, No. 2 pp. 50-56 (1997).

Gerard Said et al., "Severe Early-Onset Polyneuropathy in Insulin-Dependent Diabetes Mellitus" The New England Journal of Medicine vol. 326, No. 19, pp. 1257-1263 (1992).

Wiley W. Souba "Nutritional Support" The New England Journal of Medicine Vo. 336 No. 1. pp. 41-48 (1997).

W.A. Knaus et al., "APACHE II: A severity of disease classification system" Critical Care Medicine Vo. 13. No. 10. pp. 818-829 (1985).

D.R. Miranda et al., "Simplified Therapeutic Intervention Scoring System: The TISS-28 items-Results from a multicenter study" Crit Care Med. vol. 24, No. 1. pp. 64-73 (1996).

A. R. Keene et al, "Therapeutic Intervention Scoring System: Update 983" Crit Care Med. vol. 11. No. 1. pp. 1-3 (1983).

W.A. Knaus "Measuring the Glasgow Coma Scale In the Intensive Care Unit: Potentials and Pitfalls" Intensive Care World p. 102.

M.P. Weinstein et al., "Clinical Importance of Identifying Coagulase-Negative Staphylococci Isolated from Blood Cultures: Evaluation of The Microbiology, Epidemiology, and Outcome of Bacteremia and Fungemia In Adults" Clinical Infectious Diseases. vol. 24, pp. 584-602(1997).

C.S. Levetan et al., "Hospital Management of Diabetes" Acute Complications of Diabetes vol. 29. No. 4. pp. 745-770(2000).

J. Takala et al., "Increased Mortality Associated With Growth Hormone Treatment in Critically Ill Adults" The New England Journal of Medicine vol. 341. No. 11. pp. 785-792 (1999).

K.G.M.M. Albert et al., "Definition, Diagnosis and Classification of Diabetes Mellitus and its Complications Part 1: Diagnosis and Class-Sification of Diabetes Mellitu Provisional Report of a WHO Consultation" Diabetic Medicine vol. 15, pp. 539-543 (1998).

S.E. Capes et al., "Stress hyperglycaemia and increased risk of death after myocardial infarction in patients with and without diabetes:a Systematic overview" The Lancet vol. 355, pp. 773-778 (2000).

G.R. Bernard et al., "Efficacy and Safety of Recombinant Human Activated Protein C for Severe Sepsis" The New England Journal of Medicine V1. 344, No. 10. pp. 699-709 (2001).

E.J. Rayfield et al., "Infection and Diabetes: The Case for Glucose Control" The American Journal of Medicine vol. 72, pp. 439-450 (1982).

S.E. Geerlings et al., "Immune dysfunction in patients with diabetes mellitus (DM)" FEMS Immunology and Medical Microbiology vol. 26, pp.

A. J. Rassias et al., "Insulin Infusion Improves Neutrophil Function in Diabetic Cardia Surgery Patients" Anesth. Analg. vol. 88, pp. 1011-1016 (1999).

M.R. Losser et al., "Glucose modulates hemodynamic, metabolic, and inflammatory responses to lipopolysaccharide in rabbits" The American Physiological Society, pp. 1566-1574 (1997).

Australian and New Zealand Intensive Care Society (ANZIC) Clinical Trials Groups"Low-dose dopamine in patients with early renal Dysfunction:a placebo-controlled randomized trial" The Lancet vol. 356, pp. 2139-2143 (2000).

A. Lassnigg et al., "Lack of Renoprotective Effects of Dopamine and Furosemide during Cardiac Surgery" J. Am Soc. Nephrol vol. 11, pp. 97-104 (2000).

J. Lewis et al., "Atrial Natriuretic Factor in Oliguric Acute Renal Failure" American Journal of Kidney Diseases, vol. 36, No. 4. pp. 767-774 (2000).

Correspondence "Acute Renal Failure" The New England Journal of Medicine vol. 335. No. 17, pp. 1320-1322 (1996).

R.S. Jones et al., "Insulin's Effect on Bile Flow and Lipid Excretion During Euglycemia and Hypoglycemia" Digestive Diseases and Sciences vol. 29, No. 1, pp. 33-39 (1984).

J.J. Garcia-Marin et al., "Diabetes-Induced Cholestasis in the Rat: Possible Role of Hyperglycemia and Hypoinsulinemia" Hepatology, vol. 8, No. 2, pp. 332-340 (1988).

Per Sidenius "The Axonopathy of Diabetic Neuropathy" Diabetes, vol. 31, pp. 356-363 (1982).

A.A. Ferrando et al., "A Submaximal Dose of Insulin Promotes Net Skeletal Muscle Protein Synthesis in Patients With Severe Burns" Annals of Surgery. vol. 229, No. 1. pp. 11-18 (1999).

T.J. Orchard "From Diagnosis and Classification to Complications and Therapy" Diabetes Care, vol. 17, No. 4, pp. 326-338 (1994).

G. Hawthorne et al., "Outcome of pregnancy in diabetic women in northeaset England and in Norway, Jul. 1994" BMJ. vol. 321. pp. 730-731. (2000).

English Translation of : Iapichino et al., L'usage de l'insulin comme agent anabolisant doit-il Etre preconise chez le subject denutri ou agresse Nutr. Clin. Metabol. vol. 10, pp. 243-252.

C.F. Bolton "7.8 Acute Weakness" 7 The Neurological System, pp. 490-495, (1999).

W.A. Knaus "Measuring the Glasgow Coma Scale In the Intensive Care Unit: Potentials and Pitfalls" Intensive Care.World, vol. 11, No. 3, pp. 102, (1995).

S.E. Geerlings et al., "Immune dysfunction in patients with diabetes mellitus (DM)" FEMS Immunology and Medical Microbiology vol. 26, pp. 259-265 (1999).

English Translation of: Iapichino et al., L'usage de l'insulin comme agent anabolisant doit-il Etre preconise chez le subject denutri ou agresse Nutr. Clin. Metabol. vol. 10, pp. 243-252 (1996).

Fantus, I. George et al., Pervanadate [Peroxide(s) of Vanadate] Mimics Insulin Action in Rat Adipocytes via Activation of the Insulin Receptor Tyrosine Kinase, Biochemistry, 1989, vol. 28, pp. 8864-8871.

Swarup, Ganshyam et al., "Inhibition of Membrane Phosphotyrosyl-Protein Phosphatase Activity by Vanadate", Biochemical and Biophysical Research Communications, 1982, vol. 107, Part 3, pp. 1104-1109.

Thadhani, R. et al., "Acute Renal Failure", N. Eng. J. Med., 1996, vol. 334, pp. 1448-1460.

\* cited by examiner

METHODS AND PREPARATIONS FOR CURING CLINICALLY ILL PATIENTS

CROSS REFERENCE TO RELATED APPLICATIONS

This application is a continuation of PCT/DK01/00287 filed Apr. 30, 2001 and claims priority under 35 U.S.C. 119 of Danish application no. PA 2001 00604 filed Apr. 15, 2001; Pa 2001 00605 filed Apr. 16, 2001 and British application no. 0010856.3 filed May 5, 2000, the contents of which are fully incorporated herein by reference.

FIELD OF THE INVENTION

The present invention relates to a novel the use of blood glucose regulators, and a novel method of treating a clinically ill patient. Furthermore, the present invention relates to advertising media and material and information media and material like giving information about the novel utilities, indications and actions of these medicaments and to a method of selling these medicaments by giving information about their novel utilities, indications and actions.

BACKGROUND

A specific type of polyneuropathy develops in patients that are treated within an intensive care unit (hereinafter also designated ICU) for several days to weeks and this for a variety of primary injuries or illnesses. This polyneuropathy, known as "Critical Illness Polyneuropathy" (hereinafter also designated CIPNP) occurs in about 70% of patients who have the systemic inflammatory response syndrome (SIRS) (Zochodne D W et al. 1987 Polyneuropathy associated with critical illness: a complication of sepsis and multiple organ failure. Brain, 110: 819-842); (Leijten FSS & De Weerdt A W 1994 Critical illness polyneuropathy: a review of the literature, definition and pathophysiology. Clinical Neurology and Neurosurgery, 96: 10-19). However, clinical signs are often absent and it remains an occult problem in many ICUs worldwide. Nonetheless, it is an important clinical entity as it (is) a frequent cause of difficulty to wean patients from the ventilator and it leads to problems with rehabilitation after the acute illness has been treated and cured.

When CIPNP is severe enough, it causes limb weakness and reduced tendon reflexes. Sensory impairment follows but is difficult to test in ICU patients. Electro-physiological examination (EMG) is necessary to establish the diagnosis (Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495). This examination will reveal a primary axonal degeneration of first motor and then sensory fibers. Phrenic nerves are often involved. Acute and chronic denervation has been confirmed in muscle biopsies of this condition. If the underlying condition (sepsis or SIRS) can be successfully treated, recovery from and/or prevention of the CIPNP can be expected. This will occur in a matter of weeks in mild cases and in months in more severe cases. In other words, the presence of CIPNP can delay the weaning and rehabilitation for weeks or months.

The pathophysiology of this type of neuropathy remains unknown (Bolton C F 1996 Sepsis and the systemic inflammatory response syndrome: neuromuscular manifestations. Crit Care Med. 24: 1408-1416). It has been speculated to be directly related to sepsis and its mediators. Indeed, cytokines released in sepsis have histamine-like properties which may increase microvascular permeability. The resulting endoneural edema could induce hypoxia, resulting in severe energy deficits and hereby primary axonal degeneration. Alternatively, it has been suggested that cytokines may have a direct cytotoxic effect on the neurons. Contributing factors to disturbed microcirculation are the use of neuromuscular blocking agents and steroids. Moreover, a role for aminoglucosides in inducing toxicity and CIPNP has been suggested. However, there is still no statistical proof for any of these mechanisms in being a true causal factor in the pathogenesis of CIPNP.

Although polyneuropathy of critical illness was first described in 1985 by three different investigators, one Canadian, one American, and one French, to date there is no effective treatment to prevent or stop Critical Illness Polyneuropathy.

To date the current standard of practice of care, especially of critically ill patients, was that within the settings of good clinical ICU practice, blood glucose levels are allowed to increase as high as to 250 mg/dL or there above. The reason for this permissive attitude is the thought that high levels of blood glucose are part of the adaptive stress responses, and thus do not require treatment unless extremely elevated (Mizock B A. Am J Med 1995; 98: 75-84). Also, relative hypoglycaemia during stress is thought to be potentially deleterious for the immune system and for healing (Mizock B A. Am J Med 1995; 98: 75-84).

BRIEF SUMMARY OF THE INVENTION

This invention was based in part on the discovery that critical illness in a patient and/or CIPNP can be prevented, treated or cured, at least to a certain extent, by strictly controlling glucose metabolism during said critical illness by applying intensive treatment with a blood glucose regulator, for example, insulin treatment, with clamping of blood glucose levels within a range where the lower limit can be selected to be about 60, about 70 or about 80 mg/dL and the upper limit can be selected to be about 110, about 120 or about 130 mg/dL, more specifically to the normal range (i.e., from about 80 to about 110 mg/dL). The skilled art worker, for example, the physician, will be able to decide exactly which upper and lower limits to use. Alternatively, the range is from about 60 to about 130, preferably, from about 70 to about 120, more preferred, from about 80 to about 110 mg/dL.

This invention demonstrates that clamping of blood glucose levels within the above range, for example, within normal limits (about 80 to about 110 mg/dL) in a critically ill patient or in a chronic ill patient can be used to significantly reduce the incidence of critical illness in a patient and/or CIPNP and to lengthen the time free of critical illness in a patient and/or CIPNP in a patient that do develop this problem.

In the illustrative embodiments of present invention, blood glucose levels were controlled by insulin treatment. However after this invention, it will be clear for the man skilled in the art that also active insulin derivatives and its physiologically tolerated salts and other blood glucose regulators can be used to obtain the same outcome.

Furthermore, it will be clear for the man skilled in the art, that compounds of the group of biologically active substances having insulin releasing action can be used to treat critical illness in a patient and/or Critical Illness Polyneuropathy or to manufacture a medicine to treat critical illness in a patient and/or Critical Illness Polyneuropathy. Such compound with an activity of promoting the secretion of insulin were already well disclosed before the moment of this invention such as the Islets-Activating Proteins (Ui; Michio et al. U.S. Pat. No. 5,000,953, Mar. 19, 1991) and the glucagon-like peptides (Habener; Joel F. Newton Highlands, Mass. U.S. Pat. No. 5,614,492, Mar. 25, 1997).

Furthermore, it will be clear for the man skilled in the art, that compounds of the group of compounds that stimulate signal transduction mediated by an insulin receptor type tyrosine kinase in a cell can be used to treat or to manufacture a medicine to treat critical illness in a patient and/or Critical Illness Polyneuropathy. It was well known before the date of this invention that insulin binding to the insulin receptor triggers a variety of metabolic and growth promoting effects. Metabolic effects include glucose transport, biosynthesis of glycogen and fats, inhibition of triglyceride breakdown, and growth promoting effects include DNA synthesis, cell division and differentiation. It is known that some of these biological effects of insulin can be mimicked by vanadium salts such as vanadates and pervanadates. However, this class of compounds appears to inhibit phosphotyrosine phosphatases generally, and are potentially toxic because they contain heavy metal (U.S. Pat. No. 5,155,031; Fantus et al., 1989, Biochem., 28:8864-71; Swarup et al., 1982, Biochem. Biophys. Res. Commun. 107:1104-9). Moreover, it had been already demonstrated (LAMMERS REINER et al. Jan. 19, 1999, U.S. Pat. No. 5,861,266 & WO 9523217) that certain protein-tyrosine phosphatases (PTP's), in particular, RPTP.alpha. and RPTP.epsilon., specifically regulate the insulin receptor signalling pathway. Compounds that specifically modulate the activity of the controlling RPTP, thereby prolonging or enhancing signal transduction mediated by the insulin receptor can thus be used to treat critical illness in a patient and/or Critical Illness Polyneuropathy or to manufacture a medicine to treat critical illness in a patient and/or Critical Illness Polyneuropathy. Such compounds have low toxicity since they are specific for the PTPs associated with insulin receptor activity, and do not significantly affect the activity of other PTPs that are non-specific.

One object of the present invention is to increase the survival rate of a critically ill patient and/or a CIPNP patient.

Another object of the present invention is to find a life saving drug for a critically ill patient and/or a CIPNP patient.

A further object of the present invention is to find a life saving treatment of critically ill patients and/or a CIPNP patient.

A still further object of the present invention is to reduce the time a critically ill patient and/or a CIPNP patient, stays within an ICU.

Another object of the present invention is to shorten the time a critically ill patient and/or a CIPNP patient, stays at the hospital.

Another object of the present invention is to suppress states of CIPNP.

Another object of the present invention is to prevent and/or treat CIPNP.

Another object of the present invention is to prevent and/or treat sepsis and/or its mediators in a critically ill patient and/or in CIPNP.

Another object of the present invention is to find a medicament with an application targeted at patients at risk for suffering from CIPNP, for example when in an ICU.

Another object of the present invention is to find a medicament which can be used for prevention and/or treatment a critically ill patient and/or CIPNP.

Another object of the present invention is to treat a critically ill patient and/or a CIPNP patient, so that he is no longer in need of vital organ system support.

Another object of the present invention is to treat a critically ill patient and/or a CIPNP patient, so that it is considered sufficient for him to receive at least about two third of the caloric need through the normal enteral route.

Another object of the present invention is to reduce the risk or likelihood from multiple organ failure in a critically ill patient and/or a CIPNP patient.

Another object of the present invention is to reduce the risk or likelihood from multiple organ failure with a proven septic focus on post-mortem examination in a critically ill patient and/or a CIPNP patient.

Another object of the present invention is to reduce mortality, for example, in-hospital mortality, in a critically ill patient and/or in a CIPNP patient.

Another object of the present invention is to reduce morbidity, for example, in-hospital morbidity, in a critically ill patient and/or in a CIPNP patient.

Another object of the present invention is to reduce the use of mechanical ventilatory support to a critically ill patient and/or to a CIPNP patient.

Another object of the present invention is to reduce the likelihood of renal replacement therapy and/or renal failure in a critically ill patient and/or a CIPNP patient.

Another object of the present invention is to reduce the likelihood of disturbed kidney function parameters on a critically ill patient and/or in a CIPNP patient.

Another object of the present invention is to reduce the likelihood of hyperbilirubinemia in a critically ill patient and/or in a CIPNP patient.

Another object of the present invention is to reduce the likelihood for blood stream infections in a critically ill patient and/or in a CIPNP patient.

Another object of the present invention is to reduce the likelihood of disturbance in markers of inflammations and/or inflammatory responses in a critically ill patient, and/or in a CIPNP patient.

Another object of the present invention is to reduce the use of antibiotics in a critically ill patient and/or in a CIPNP patient.

Another object of the present invention is to reduce the likelihood of a critically ill patient and/or in a CIPNP patient having repetitive positive EMGs.

Another object of the present invention is to reduce the amount of red cell transfusion to a critically ill patient and/or to a CIPNP patient.

Another object of the present invention is to prevent or reduce the amount of ultimately futile intensive care to a critically ill patient and/or to a CIPNP patient.

Another object of the present invention is to protect a critically ill patient and/or in a CIPNP patient from cholestasis.

Another object of the present invention is to reduce the need for invasive treatment in a critically ill patient and/or in a CIPNP patient.

Another object of the present invention is to reduce the stress induced hyperglycaemia in a critically ill patient and/or in a CIPNP patient.

DETAILED DESCRIPTION OF THE INVENTION

Definitions

Figure 1:
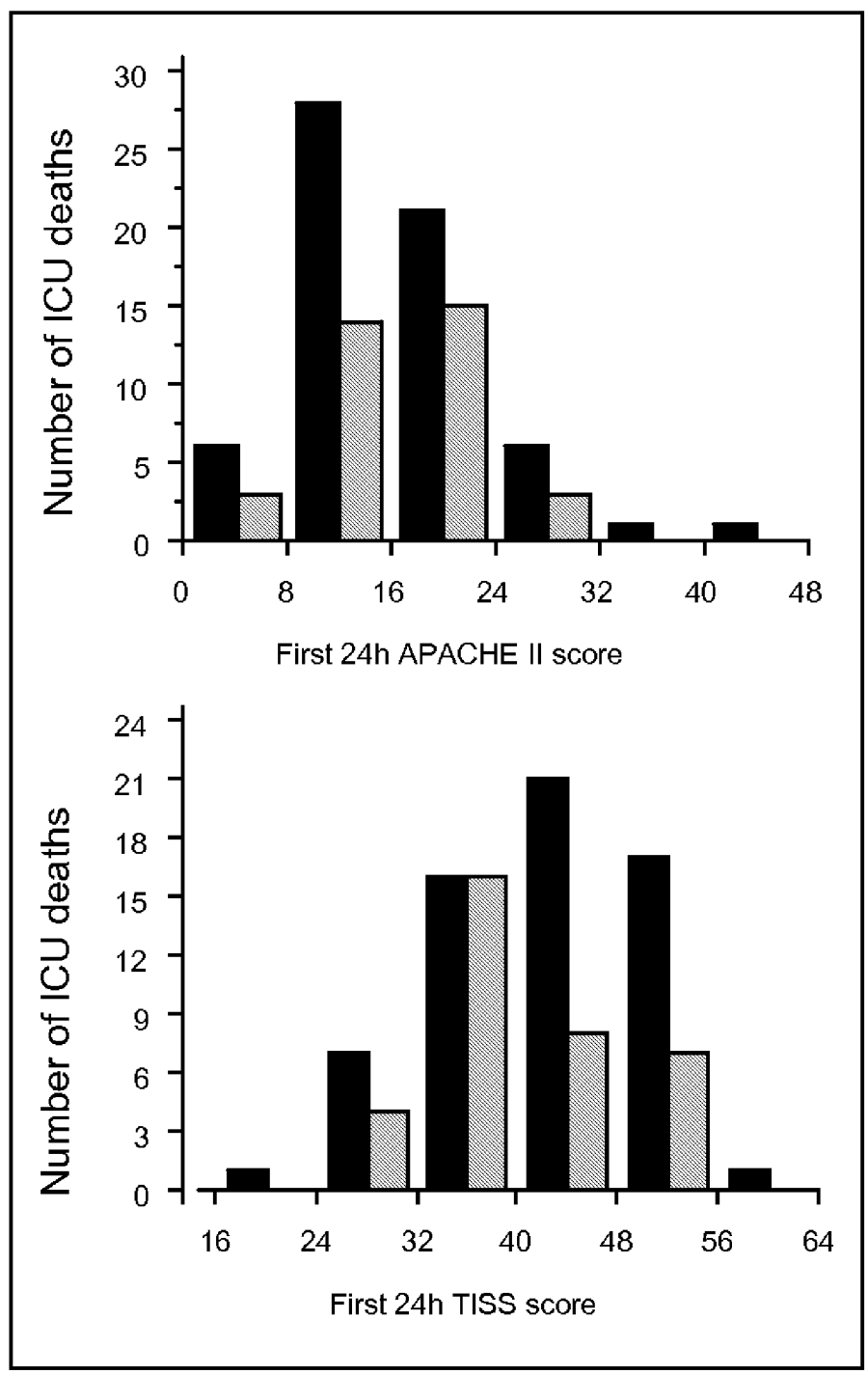
FIG. 1 shows ICU deaths in different strata of first 24h-APACHE II and TISS scores. APACHE denotes Acute Physiology and Chronic Health Evaluation. TISS denotes Therapeutic Intervention Scoring System. Filled bars represent deaths in the RIS group and hatched bars the deaths in the IIS group.

The term "systemic inflammatory response syndrome (SIRS)", as used herein refers to the uncontrolled disease process which ensues an initial insult and which gives rise to a multisystem disturbance secondary to inflammatory mediators released during shock.

The term "sepsis", as used herein refers to "SIRS", as described above, which is particularly caused by an infectious insult leading to the initial shock phase.

The term "mediators of sepsis", as used herein refers to factors released by inflammatory cells, such as TNFs, interleukins, bradykinins etc.

The term "insulin receptor type tyrosine kinase", as used herein refers to a post-receptor signal transduction pathway involved in the insulin signaling.

The term "endoneural edema", as used herein refers to swelling of the neuronal cells.

The term "phrenic nerves", as used herein refers to the left and right nervus phrenicus, innervating the diaphragm.

The term "blood glucose regulator", as used herein refers to any compound which is able to regulate the blood glucose level. Examples of blood glucose regulators are insulin, active insulin derivatives, insulin analogues, compounds that stimulate signal transduction mediated by an insulin receptor type tyrosine kinase in a cell, certain protein-tyrosine phosphatases (PTP's), other type II antidiabetica, and other biologically active substances having insulin releasing action.

The term "insulin", as used herein refers to insulin from any species such as porcine insulin, bovine insulin, and human insulin and salts thereof such as zinc salts, and protamin salts.

The term "active derivatives of insulin", as used herein are what a skilled art worker generally considers derivatives, vide general textbooks, for example, insulin having a substituent not present in the parent insulin molecule.

The term "insulin analogues", as used herein refers to insulin wherein one or more of the amino acid residues have been exchanged with another amino acid residue and/or from which one or more amino acid residue has been deleted and/or from which one or more amino acid residue has been added with the proviso that said insulin analogue has a sufficient insulin activity. Using results from the so-called free fat cell assay, any skilled art worker, for example, a physician, knows when and which dosages to administer of the insulin analogue. Examples of insulin analogues are described in the following patents and equivalents thereto: U.S. Pat. No. 5,618,913, EP 254,516, EP 280,534, U.S. Pat. Nos. 5,750, 497, and 6,011,007. Examples of specific insulin analogues are insulin aspart (i.e., $Asp^{B28}$ human insulin), insulin lispro (i.e., $Lys^{B28}$, $Pro^{B29}$ human insulin), and insulin glagin (i.e., $Gly^{A21}$, $Arg^{B31}$, $Arg^{B32}$ human insulin).

Also compounds which can be considered being both an insulin derivative and an insulin analogue can be used to practice the present invention. Examples of such compounds are described in the following patents and equivalents thereto: U.S. Pat. Nos. 5,750,497, and 6,011,007. An example of a specific insulin analogues and derivatives is insulin detenir (i.e., des-$Thr^{B30}$ human insulin γ $Lys^{B29}$ tetradecanoyl).

The term "non-diabetic patient", as used herein refers to a patient who has not been diagnosed as having diabetes.

In its broadest sense, the term a "critically ill patient" (herein designated CIP), as used herein refers to a patient who has sustained or are at risk of sustaining acutely life-threatening single or multiple organ system failure due to disease or injury, a patient who is being operated and where complications supervene, and a patient who has been operated in a vital organ within the last week or has been subject to major surgery within the last week. In a more restricted sense, the term a "critically ill patient", as used herein refers to a patient who has sustained or are at risk of sustaining acutely life-threatening single or multiple organ system failure due to disease or injury, or a patient who is being operated and where complications supervene. In an even more restricted sense, the term a "critically ill patient", as used herein refers to a patient who has sustained or are at risk of sustaining acutely life-threatening single or multiple organ system failure due to disease or injury. Similarly, these definitions apply to similar expressions such as "critical illness in a patient" and a "patient is critically ill".

The term "Intensive Care Unit" (herein designated ICU), as used herein refers to the part of a hospital where critically ill patients are treated. Of course, this might vary from country to country and even from hospital to hospital and said part of the hospital may not necessary, officially, bear the name "Intensive Care Unit" or a translation or derivation thereof. Of course, the term "Intensive Care Unit" also covers a nursing home, a clinic, for example, a private clinic, or the like if the same or similar activities are performed there.

Treatment Methods of the Invention

Usually and preferably, the treatment of a critical ill patent necessitates prolonged minute-to-minute therapy and/or observation, usually and preferably in an intensive care unit (ICU) or a special hospital unit, for example, a post operative ward or the like which is capable of providing a high level of intensive therapy in terms of quality and immediacy.

Examples of a critically ill patient is a patient in need of cardiac surgery, cerebral surgery, thoracic surgery, abdominal surgery, vascular surgery, or transplantation, or a patient suffering from neurological diseases, cerebral trauma, respiratory insufficiency, abdominal peritonitis, multiple trauma, severe burns, or CIPNP.

The glucose metabolism of the a clinical ill patient may be controlled by clamping the blood glucose level within the ranges mentioned in connection with the present invention. Any skilled art worker, for example, a physician, knows how to do this, for example using insulin or another blood glucose regulator. Any skilled art worker is able to find the pharmaceutically effective amount of the blood glucose regulator used and to determine how often it is to be administered. Specific reference can be made to brochures concerning regulation of the blood glucose level, available from Novo Nordisk A/S, and a huge number of other publications.

Conveniently, the blood glucose level is kept within the ranges mentioned in connection with the present invention for as long a period of time as the patient is critically ill. Hence, as a general rule, the blood glucose level is kept within the ranges mentioned in connection with the present invention as long as the patient is critically ill. Consequently, the blood glucose level is usually kept within the ranges mentioned in connection with the present invention for a period of time of more than about 8 hours, preferably more than about 24 hours, even more preferred more than about 2 days, especially more than about 4 days, and even more than about 7 days. In certain cases, it may even be preferred that the blood glucose level is kept within the ranges mentioned in connection with the present invention after the patient (previously) considered as being critically ill has been transferred from the Intensive Care Unit to another part of the hospital or even after said patient has left the hospital.

A critical ill patient, optionally entering an ICU, may be fed continuously, on admission with mainly intravenous glucose (for example, about 200 g to about 300 g per 24 hours) and from the next day onward with a standardised feeding schedule aiming for a caloric content up to between about 10 and about 40, preferably between about 20 and about 30, non-protein Calories/kg/24 hours and a balanced composition (for example, between about 0.05 and about 0.4, preferably between about 0.13 and about 0.26, g nitrogen/kg/24 hours and between about 20% and about 40% of non-protein Calories as lipids) of either total parenteral, combined parenteral/enteral or full enteral feeding, the latter mode attempted as early as possible. Other comcomitant ICU therapy can be left to the discretion of attending physicians.

Alternatively, the following procedure can be used or it is possible to use a combination or variant of these procedures, as the physician considers advantageous for the patient:

A critical ill patient may be fed, on the admission day, using, for example, a 20% glucose infusion and from day 2 onward by using a standardised feeding schedule consisting of normal caloric intake (for example, about 25-35 Calories/kgBW/24 h) and balanced composition (for example, about 20%-40% of the non-protein Calories as lipids and about 1-2 g/kgBW/24 h protein) of either total parenteral, combined parenteral/enteral or full enteral feeding, the route of administration of feeding depending on assessment of feasibility of early enteral feeding by the attending physician. All other treatments, including feeding regimens, were according to standing orders currently applied within the ICU.

The present invention also relates to advertising media and material and information media and material containing or giving information about the novel utility, indication, and action of the blood glucose regulators according to the present invention. Examples of advertising media and material and information media and material a brochure, packaging material which is used for the customer package such as the outer box, the inner box, or a blisterpack, any printed material/leaflet supplied with the drug such as a package insert, a patient leaflet, or patient information, a label, a web site, a movie, an advertising movie, a video, and the like. Any skilled art worker knows how to manufacture the above advertising media and material and information media and material. An example of a brochure according to the present invention is a brochure in which it is stated (or suggested) that insulin can be used to treat CIPNP patients, for example in a ICU.

An advertisement according to the present invention could have the following text:

--- to physicians, especially those working in an Intensive Care Unit:
LIFE SAVING TREATMENT In order to save life, it is important that the blood glucose level of a critically ill patient is kept within the range from about 80 to about 110 mg/dL. This can be done by using insulin preparations from Novo Nordisk A/S. [More information will be available from www.novonordisk.com.]

---

Furthermore, the present invention relates to a method of selling a blood glucose regulator by giving information about their novel utility, novel activity and/or novel pharmaceutical indications described herein. One method of selling a blood glucose regulator could be by telling a person, for example, a physician, that insulin can be used to treat CIPNP patients, for example in a ICU. Alternatively, a method of selling a blood glucose regulator could be by distributing the above advertising and information media are brochures such as packaging material which is used for the customer package, any printed material/leaflet supplied with the drug, or patient information, labels, web sites, movies, advertising movies, videos, and the like. Another method of selling a blood glucose regulator which is covered by the present claims is to support a speaker giving information about the novel utility, indication, and action of the blood glucose regulators according to the present invention or to support an author writing an article giving information about the novel utility, indication, and action of the blood glucose regulators according to the present invention. Other variations hereof will be obvious for the skilled art worker, for example distributing an advertisement as the above.

According to one embodiment, the present invention relates to a use of a blood glucose regulator for the manufacture of a life saving drug to treat or cure a critically ill patient and/or a CIPNP-patient and/or a potential CIPNP-patient.

According to another embodiment, the present invention relates to a use of a blood glucose regulator for the manufacture of a medicament to treat or cure a critically ill patient and/or a CIPNP-patient and/or a potential CIPNP-patient.

According to a further embodiment, the present invention relates to a use of a blood glucose regulator for the manufacture of a medicament to prevent than a patient becomes critical ill or develops CIPNP.

According to a further embodiment, the present invention relates to a use of a blood glucose regulator for the manufacture of a medicament to increasing the survival rate of a critically ill patient and/or a CIPNP-patient and/or a potential CIPNP-patient.

According to a further embodiment, the present invention relates to a use of a blood glucose regulator for the manufacture of a medicament to reducing the time a critically ill patient and/or a CIPNP-patient and/or a potential CIPNP-patient stays within a hospital, for example stays within an ICU.

According to a further embodiment, the present invention relates to a use of a blood glucose regulator for the manufacture of a medicament to prevent, treat or cure SIRS, especially in a critically ill patient and/or a CIPNP-patient and/or a potential CIPNP-patient.

According to a further embodiment, the present invention relates to a use of a blood glucose regulator for the manufacture of a medicament to prevent, treat or cure sepsis and/or its mediators, especially in a critically ill patient and/or a CIPNP-patient and/or a potential CIPNP-patient.

According to a further embodiment, the present invention relates to a use of a blood glucose regulator for the manufacture of a medicament to reduce mortality, hospitality stay, bacteraemia, need for dialysis and need for ventilatory support in a critically ill patient and/or a CIPNP-patient and/or a potential CIPNP-patient.

According to a further embodiment, the present invention relates to a use of a blood glucose regulator for the manufacture of a medicament to treat a critically ill patient and/or a CIPNP-patient and/or a potential CIPNP-patient so that he is no longer in need of vital organ system support or to treat a critically ill patient and/or a CIPNP-patient or and/a potential CIPNP-patient so that it is considered sufficient for him to receive at least about two third of the caloric need through the normal enteral route to reduce the risk or likelihood from multiple organ failure, to reduce the risk or likelihood from multiple organ failure with a proven septic focus on post-mortem examination, to reduce mortality, for example, in-hospital mortality, to reduce the use of mechanical ventilatory support, to reduce the likelihood of renal replacement therapy and/or renal failure, to reduce the likelihood of disturbed kidney function parameters, to reduce the likelihood of hyper-bilirubinemia, to reduce the likelihood for blood stream infections, to reduce the likelihood of disturbance in markers of inflammations and/or inflammatory responses, to reduce the use of antibiotics, to reduce the amount of red cell transfusion, or to reduce the stress induced hyperglycaemia of, in, or to a critically ill patient and/or in a CIPNP-patient or and/a potential CIPNP-patient or to reduce the likelihood of a critically ill patient and/or in a CIPNP-patient and/or a potential CIPNP-patient having repetitive positive EMGs or to prevent or reduce the amount of ultimately futile intensive care to a critically ill patient and/or to a CIPNP-patient or and/a potential CIPNP-patient or to protect a critically ill patient and/or in a CIPNP-patient or and/a potential CIPNP-patient from cholestasis or to reduce the need for invasive treatment in a critically ill patient and/or in a CIPNP-patient or and/a potential CIPNP-patient or any condition of insulin resistance leading to hyperinsulinimea in combination with hyperglycaemia in a critically ill patient and/or in a CIPNP-patient or and/a potential CIPNP-patient.

According to a further embodiment, the present invention relates to the novel uses described herein, wherein the blood glucose regulator is insulin, active insulin derivatives, insulin analogues, compounds that stimulate signal transduction mediated by an insulin receptor type tyrosine kinase in a cell, certain protein-tyrosine phosphatases (PTP's), other type II antidiabetica, and other biologically active substances having insulin releasing action.

According to a further embodiment, the present invention relates to the novel use described herein, wherein the blood glucose regulator is a blood glucose regulator which is not to be administered orally.

According to a further embodiment, the present invention relates to the novel uses described herein, wherein the blood glucose regulator is used in such a way that the blood glucose level is kept within a range where the lower limit is about 60, about 70 or about 80 mg/dL and the upper limit is about 110, about 120 or about 130 mg/dL, preferably kept in a range from about 80 to about 110 mg/dL).

According to a further embodiment, the present invention relates to the novel uses described herein, wherein the blood glucose regulator is used in such a way that the blood glucose level is kept within the range from about 60 to about 130, preferably, from about 70 to about 120, more preferred, from about 80 to about 110 mg/dL.

According to a further embodiment, the present invention relates to the novel uses described hefrein, wherein the blood glucose level is kept within the ranges mentioned above for a period of time of more than about 8 hours, preferably more than about 24 hours, even more preferred more than about 2 days, especially more than about 4 days, and even more than about 7 days.

According to a further embodiment, the present invention relates to the novel uses described herein, wherein the patient to be treated is a mammal, preferably a human (being).

According to a further embodiment, the present invention relates to the novel uses described herein, wherein the patient is a non-diabetic patient.

According to a further embodiment, the present invention relates to the novel uses described herein, wherein the patient is a patient in need of cardiac surgery, cerebral surgery, thoracic surgery, abdominal surgery, vascular surgery, or transplantation, or a patient suffering from neurological diseases, cerebral trauma, respiratory insufficiency, abdominal peritonitis, multiple trauma, severe burns, or CIPNP.

According to a further embodiment, the present invention relates to a novel method for the treatment, curing or prevention as described herein, wherein the patient to be treated receives an effective amount of the compound mentioned above and as stated above.

According to a further embodiment, the present invention relates to novel advertising media and material and information media and material having or giving information about the indications and utilities of a blood glucose regulator described herein and in the way described above.

According to a further embodiment, the present invention relates to a novel method of selling a blood glucose regulator by giving information of about the indications and utilities of said blood glucose regulator described herein and in the way described herein.

A further, specific embodiment of the present invention relates to the novel use of a pharmaceutically effective composition for use in the therapeutic treatment of a mammal having Critical Illness Polyneuropathy, comprising a pharmaceutically effective amount of a compound which is selected from a group of compounds comprising insulin, its active derivatives and the physiologically tolerated salts of these insulin derivatives or of a group of biologically active substances having insulin releasing action or of a group of compounds that stimulate signal transduction mediated by an insulin receptor type tyrosine kinase in a cell.

Another specific embodiment of the present invention relates to the novel use of a pharmaceutically effective composition for use in the prophylactic treatment of a mammal having Critical Illness Polyneuropathy, comprising a pharmaceutically effective amount of a compound which is selected from a group of compounds comprising insulin, its active derivatives and the physiologically tolerated salts of these insulin derivatives or of the group of biologically active substances having insulin releasing action or of the group of compounds that stimulate signal transduction mediated by an insulin receptor type tyrosine kinase in a cell.

A further embodiment of the present invention relates to the novel use of compounds of the group of compounds comprising insulin, its active derivatives and the physiologically tolerated salts of these insulin derivatives or of a group of biologically active substances having insulin releasing action or of a group of compounds that stimulate signal transduction mediated by an insulin receptor type tyrosine kinase in a cell for the manufacturing of a medicament for the treatment or prevention of Critical Illness Polyneuropathy.

A still further embodiment of the present invention relates to a novel method for the treatment of Critical Illness Polyneuropathy in mammals, wherein said critical ill individual (or patient) receives an effective amount of a compound to keep the blood glucose levels between 80 and 110 mg/dL (4.6-6.1 mmol/L), i.e., in reality or in practice between about 80 and about 110 mg/dL (i.e., between about 4.6 and about 6.1 mmol/L).

Another specific embodiment of the present invention relates to the novel method described in the previous paragraph (wherein CIPNP is treated with a compound to keep the blood glucose levels between 80 and 110 mg/dL) whereby said compound is selected from a group of compounds comprising insulin, its active derivatives and the physiologically tolerated salts of these insulin derivatives or of a group of biologically active substances having insulin releasing action or of a group of compounds that stimulate signal transduction mediated by an insulin receptor type tyrosine kinase in a cell.

In a further preferred embodiment of the present invention, the critical ill patient is a patient in need of cardiac surgery.

In another preferred embodiment of the present invention, the critical ill patient is a patient in need of cerebral surgery.

In a further preferred embodiment of the present invention, the critical ill patient is a patient in need of thoracic surgery.

In a further preferred embodiment of the present invention, the critical ill patient is a patient in need of abdominal surgery.

In a further preferred embodiment of the present invention, the critical ill patient is a patient in need of vascular surgery.

In a further preferred embodiment of the present invention, the critical ill patient is a patient in need of transplantation.

In a further preferred embodiment of the present invention, the critical ill patient is a patient suffering from neurological diseases.

In a further preferred embodiment of the present invention, the critical ill patient is a patient suffering from cerebral trauma.

In a further preferred embodiment of the present invention, the critical ill patient is a patient suffering from respiratory insufficiency.

In a further preferred embodiment of the present invention, the critical ill patient is a patient suffering from abdominal peritonitis.

In a further preferred embodiment of the present invention, the critical ill patient is a patient suffering from multiple trauma.

In a further preferred embodiment of the present invention, the critical ill patient is a patient suffering from severe burns.

In a further preferred embodiment of the present invention, the critical ill patient is a patient suffering from CIPNP.

In a further preferred embodiment of the present invention, the critical ill patient is a patient being mechanically ventilated.

EXAMPLES

The terminology used herein is for the purpose of describing particular embodiments only, and is not intended to limit the scope of the present invention which will be limited only by the appending claims. This invention is not limited to the particular methodology, protocols, delivery forms and reagents described as these may vary.

Example 1

Material and Methods

In a prospective clinical study, we tested the hypothesis that the incidence of CIPNP can be reduced by more strict metabolic using intensive insulin treatment from admission onward. Between Feb. 2 and Apr. 25, 2000, 400 patients were included in the study. They had been randomly allocated to one of two insulin (Actrapid H M NovoLet of Novo Nordisk) treatment schedules:

(1) insulin infusion started at a dose of 1 U/h only when blood glucose is >230 mg/dL (13 mmol/L) and titrated up (2 to 4 hourly controls of blood glucose levels) with increments of 0.5 to 1 U/h to keep blood glucose below this level [180-200 mg/dL (10.3-11.2 mmol/L)]. When blood glucose levels reach 180 mg/dL, insulin infusion is stopped.

(2) insulin infusion started when blood glucose is >120 mg/dL (6.8 mmol/L) at a dose of 2 U/h and titrated up (2 to 4 hourly controls of blood glucose levels) with increments adequate to keep blood glucose levels normal and thus below this level [80-110 mg/dL (4.6-6.1 mmol/L)]. Maximal hourly insulin dose is set at 60 U per hour. When blood glucose levels reach 80 mg/dL, insulin infusion is tapered and eventually stopped until normal levels are again reached. During interruption of enteral tube feeding for determination of residual stomach content, insulin infusion is reduced proportionately to the reduction of caloric intake.

(3) Concomitantly, patients were fed, on the admission day using a 20% glucose infusion and from day 2 onward by using a standardised feeding schedule consisting of normal caloric intake (25-35 Calories/kgBW/24 h) and balanced composition (20%-40% of the non-protein Calories as lipids & 1-2 g/kgBW/24 h protein) of either total parenteral, combined parenteral/enteral or full enteral feeding, the route of administration of feeding depending on assessment of feasibility of early enteral feeding by the attending physician. All other treatments, including feeding regimens, were according to standing orders currently applied within the ICU.

Exclusion criteria were age <18y, pregnancy and not being intubated at admission.

When patients were still treated in the ICU after 7 days, a weekly EMG examination was performed to screen for the presence of CIPNP. The EMGs were always interpreted by the same expert in electrophysiology. In order to accurately assess ICU stay, which is often determined by other factors than the patient's condition—e.g. bed availability on the wards—"end of ICU stay" was defined as the day on which the attending physician considers the patient to be "ready for discharge".

Results 83 patients ended up being treated on the ICU for at least one week and were screened by EMG for the presence of CIPNP. In the group randomised into the "intensive insulin schedule", 38 patients stayed for more than 7 days and in the group randomised into the "restrictive insulin schedule", 45 patients stayed more than 7 days. Fifteen out of 38 long-stay ICU patients in the intensive insulin group (or 39% of the long stayers) revealed a positive EMG for CIPNP at any time during the ICU stay versus 30 out of 45 in the restrictive insulin group (or 67%) (P=0.01 with Chi-square). In the intensive insulin group, the mean+SD number of positive EMGs for CIPNP per patient was 0.9±1.8 (median of zero) versus 1.8±2.1 (median of 1) in the restrictive insulin group (P=0.015 with Mann-Whitney U test).

Long-stay patients in the intensive insulin group had a CIPNP-free time on the ICU of 2.1±1.8 weeks versus 1.1±1.2 weeks in the restrictive insulin group (P=0.004 with unpaired Student's t-test).

ICU-mortality was not detectably different between the two treatment groups (P=0.4).

Conclusions

This study revealed that strict metabolic control with intensive insulin treatment and clamping of blood glucose levels within normal limits significantly reduces the incidence of CIPNP and lengthens the time free of CIPNP in patients that do develop this problem. This is the first study to point to a preventive strategy for this frequently occurring and important problem in ICU patients. Since the presence of EMG-proven CIPNP has been shown to extend the need for ICU support and to prolong the time required for rehabilitation, this treatment will lead to a reduction in need for ICU support and to a shorter time for rehabilitation, which could reflect a major reduction in costs.

Example 2

A Prospective, Randomized, Controlled Study was Performed

All mechanically ventilated, adult patients admitted to the intensive care unit (ICU) were eligible for inclusion. Only 5 patients participating in another trial and 9 who were moribund or DNR coded at ICU admission were excluded. At admission, patients were randomized to either strict normalization of glycemia (4.5-6.1 mmol/L) with continuously infused insulin during intensive care, the 'intensive insulin schedule' (IIS), or the currently used 'restrictive insulin schedule' (RIS), with insulin started when blood glucose exceeds 12 mmol/L in which case glycemia is clamped to 10-12 mmol/L. An interim safety analysis revealed a difference in mortality, and the study was ended for ethical reasons.

Results

A total of 1548 patients were included, 765 in the IIS group, 783 in the RIS group, well matched at inclusion. IIS reduced ICU mortality by 43% (P=0.005) [63 deaths in the RIS group versus 35 in the IIS group; death odds ratio for IIS, corrected for all baseline univariate predictors of ICU death, was 0.52 (0.33-0.82), P=0.004] and hospital mortality by 34% (P=0.01). Mortality reduction occurred exclusively in long-stay ICU patients and was due to prevention of death from multiple organ failure with sepsis. IIS also reduced the incidence of blood stream infections, renal failure, anemia and critical illness polyneuropathy as well as the need for dialysis or hemofiltration, red cell transfusion, prolonged mechanical ventilatory support and intensive care.

Conclusion

The data suggest that disturbances in glucose metabolism during critical illness are not "adaptive and beneficial" since strict metabolic control with exogenous insulin substantially reduces morbidity and mortality.

More detailed, the study was as follows:

Study Population

All mechanically ventilated, adult (age>18y) patients admitted to our 56-bed, mainly surgical, ICU from Feb. 2, 2000 onward were considered eligible for inclusion. Only 5 patients taking part in other outcome trials and 9 who were moribund or "do not resuscitate"—coded at ICU admission were excluded. Informed consent was obtained from the closest family member. The study protocol was approved by the Institutional Review Board of the Catholic University of Leuven School of Medicine.

Study design and treatment protocols: t ICU admission, patients were randomized to either strict control of glycemia below 6.1 mmol/L (110 mg/dL) with continuously infused insulin, the 'intensive insulin schedule' (IIS), or the currently used 'restrictive insulin schedule' (RIS), with insulin started when blood glucose exceeds 12 mmol/L (215 mg/dL). In the RIS group, intravenous insulin drip, consisting of 50 IU insulin (Actrapid HM®, Novo Nordisk, Denmark) in a 50 mL NaCl 0.9% containing PERFUSOR® syringe driven by a Perfusor FM® pump (B. Braun, Melsungen, Germany), was initiated at 1 IU/h. By 2-4 hourly measurements of whole blood glucose levels in undiluted arterial blood samples using the ABL700 analyser (Radiometer Medical A/S, Copenhagen, Denmark), insulin dose was adjusted to clamp glycemia between 10-12 mmol/L.

In the IIS group, insulin drip was started at 2 IU/h when blood glucose exceeded 6.1 mmol/L. By 2-4 hourly measurements—and in case of difficult control by hourly measurements—of blood glucose levels, insulin dose was adjusted to clamp glycemia between 4.5-6.1 mmol/L. Maximal dose of insulin was arbitrarily set at 50 U/h. At ICU discharge, a restrictive insulin schedule was adopted (glycemia≦12 mmol/L) to avoid hypoglycemia in the less well controlled setting of a regular ward.

Consecutive patients were randomly assigned to one of these two treatment groups using blinded envelopes, stratified according to type of critical illness diagnosed on admission [(a) neurological disease, cerebral trauma or surgery; (b) cardiac surgery; (c) thoracic surgery and/or respiratory insufficiency; (d) abdominal surgery/peritonitis; (e) vascular surgery; (f) multiple trauma or severe burns: (g) organ transplantation; (h) others, mainly extensive oncological procedures] and balanced with the use of permuted blocks of ten.

All patients were fed continuously, on admission with mainly intravenous glucose (200-300 g/24 h) and from the next day onward with a standardised feeding schedule aiming for a caloric content up to 20-30 non-protein Calories/kg/24 h and a balanced composition (0.13-0.26 g nitrogen/kg/24 h and 20%-40% of non-protein Calories as lipids) of either total parenteral, combined parenteral/enteral or full enteral feeding, the latter mode attempted as early as possible. Other comcomitant ICU therapy was left to the discretion of attending physicians.

Baseline Assessment and Data Collection

At baseline, demographic, diagnostic and therapeutic information as well as information necessary to determine severity of illness and utilization of ICU resources were obtained from each patient (Table 1). These included APACHE-II (Acute Physiology and Chronic Health Evaluation) score with higher values indicating more severe illness (see Knaus) and simplified Therapeutic Intervention Scoring System (TISS-28) with higher values indicating a higher number of therapeutic interventions (see Reis Miranda & Keene). APACHE II and TISS scores were calculated daily from ICU admission to discharge or death.

The 'on-admission' APACHE II score was calculated from data gathered during 24 h after admission to the ICU and omitted values from stabilization in the emergency department or recovery room prior to transfer. Because of ICU bed shortage, this period outside ICU often took more than 24 h which caused a substantial treatment effect and thus lowered APACHE II scores. Moreover, zero points were usually assigned for the neurological evaluation section (Glasgow Coma Score, with higher values indicating more impaired consciousness) as the majority of patients were sedated upon ICU admission which makes correct consciousness scoring impossible. This approach is the most consistent and objective but inevitably reduces APACHE II (see Knaus).

A blood sample was taken upon ICU admission and daily at 06:00 h until discharge from ICU or death. On-admission and daily morning, whole blood glucose level as well as daily maximal and minimal glycemia were analysed. Analyses on the 06:00 h sample also included clinical chemistry, hematology and markers of inflammation.

Blood cultures were taken whenever continuously monitored central body temperature acutely rose above 38.5° C. Results from all blood cultures were interpreted by the same blinded investigator. An episode of bacteremia, fungemia or mycobacteremia was defined by the first positive blood culture in a series. To identify a blood stream infection with coagulase-negative staphylocci, identical strains (compared by antibiogram) of microorganisms in two or more positive blood cultures were required (see Weinstein 1997 and Weinstein 1998).

In patients treated in ICU for more than one week, a weekly electromyography (EMG) was performed to screen for Critical Illness Polyneuropathy. EMGs were interpreted by the same electrophysiologist who was blinded for randomization. In case of ICU death, a post-mortem examination was performed to confirm the presumed cause of death. The pathologists were also blinded for the insulin treatment schedule.

Outcome Measures:

The primary outcome measure was death from all causes during intensive care. Secondary outcome measures were in-hospital mortality, incidence of prolonged intensive care dependency and need for ICU re-admission, need for vital organ system support comprising mechanical ventilatory support, renal replacement therapy (continuous or intermittent hemofiltration or dialysis), inotropic or vasopressor support, incidence of critical illness polyneuropathy, the degree of inflammation, incidence of blood stream infections and use of antibiotics, transfusion requirements and incidence of hyperbilirubinemia. Furthermore, use of intensive care resources was analysed by cumulative TISS scores. In order to accurately and objectively assess duration of ICU stay, which is often influenced by non-patient related factors such as bed availability on regular wards, patients were defined 'dischargable from ICU' when they were no longer in need of vital organ system support and received at least ⅔rd of the caloric need through the normal enteral route or earlier when actually sent to a ward.

Statistical Analysis:

We hypothesized to detect a difference in mortality selectively in long-stay (>5 days) critically ill patients. Since prolonged ICU stay is not predictable at ICU admission, and since we aimed at treatment from admission onward, we chose to include all mechanically ventilated patients admitted to the ICU, without selection. We estimated that inclusion of 2500 admissions would be needed to rule out an absolute difference in mortality of ±5% in the long-stay cohort which would translate in an absolute risk reduction of ±2% for overall ICU mortality (2-sided alfa level of <0.05). Three-monthly interim analyses of overall ICU mortality were performed with stopping bounderies (with a 2-sided alfa-level of <0.01) designed to allow early study termination if one of the intervention groups was found to be clearly inferior. Interim analysis after one year of study revealed a significantly higher number of deaths in the RIS group, after which the study was ended for ethical reasons. All analyses were done on intention to treat basis.

Baseline and outcome variables were compared using Student's t-test, Chi-square test and Mann-Whitney-U test, as appropriate. Death odds ratios were calculated using multivariate logistic regression analysis. The effect on time of in-hospital death was assessed by Kaplan-Meier analysis and logrank (Mantel-Cox) significance testing. Patients discharged from the hospital were considered as survivors. Data are presented as percentages, means ±SD or medians ($25^{th}$-$75^{th}$ percentile) unless indicated otherwise.

Results

Study Population:

The study involved 1548 patients, 783 in the RIS group and 765 in the IIS group, well matched at randomization (Table 1) although IIS patients tended to be slightly older and more obese compared with RIS patients.

A history of diabetes was present in 13.2% of patients, 4.6% treated with subcutaneous insulin injections, 8.6% receiving oral anti-diabetic treatment. On ICU admission, 74.6% of patients revealed glycemia higher than normal when compared with overnight fasted reference values ($\geq 6.1$ mmol/L) and 56% had a blood glucose level higher than the fasted diabetes threshold ($\geq 7$ mmol/L). Only 11.7%, however, revealed an on-admission glycemia in the non-fasting diabetes range ($\geq 11$ mmol/L). A non-fasting "diabetic" glycemia on ICU admission did not correlate well with having a history of diabetes, as only 19.6% of the known diabetics revealed a blood glucose level on ICU admission $\geq 11$ mmol/L. The two study groups were comparable for diabetes diagnosed before ICU admission and for incidence of on-admission hyperglycemia (Table 1).

Glycemia Control:

Mean and maximal amount of non-protein Calories per patient (not including the first and last day of ICU stay) was 19±7 kCal/kg/24 h and 24±10 kCal/kg/24 h, respectively. Mean and maximal amount of dietary nitrogen was 0.14±0.06 gN/kg/24 h and 0.19±0.08 gN/kg/24 h, respectively. Daily amounts and composition of the feeding regimens were comparable in the two groups.

In the IIS group, 99% of patients required exogenous insulin, a need which persisted for the entire duration of ICU stay (Table 2). Glycemia was well controlled with mean morning levels of 5.8±1.0 mmol/L. Only 0.1% of IIS patients had blood glucose levels that failed to go below 6.1 mmol/L within 48 h, 48% never exceeded 6.1 mmol/L after treatment initiation and only 17% occasionally peaked over 8.4 mmol/L. Mean morning glycemia in the RIS group was 8.5±1.8 mmol/L. Only 39% of RIS patients actually received insulin and those revealed a mean morning glycemia of 9.6±1.8 mmol/L in contrast to 7.8±1.4 mmol/L in the non-insulin requiring RIS patients.

In 39 IIS-treated patients, glycemia transiently fell below 2.3 mmol/L versus 6 patients in the RIS group. Such an event of hypoglycemia was always quickly corrected and never induced serious symptoms such as hemodynamic deterioration or epilepsia.

Figure 2:
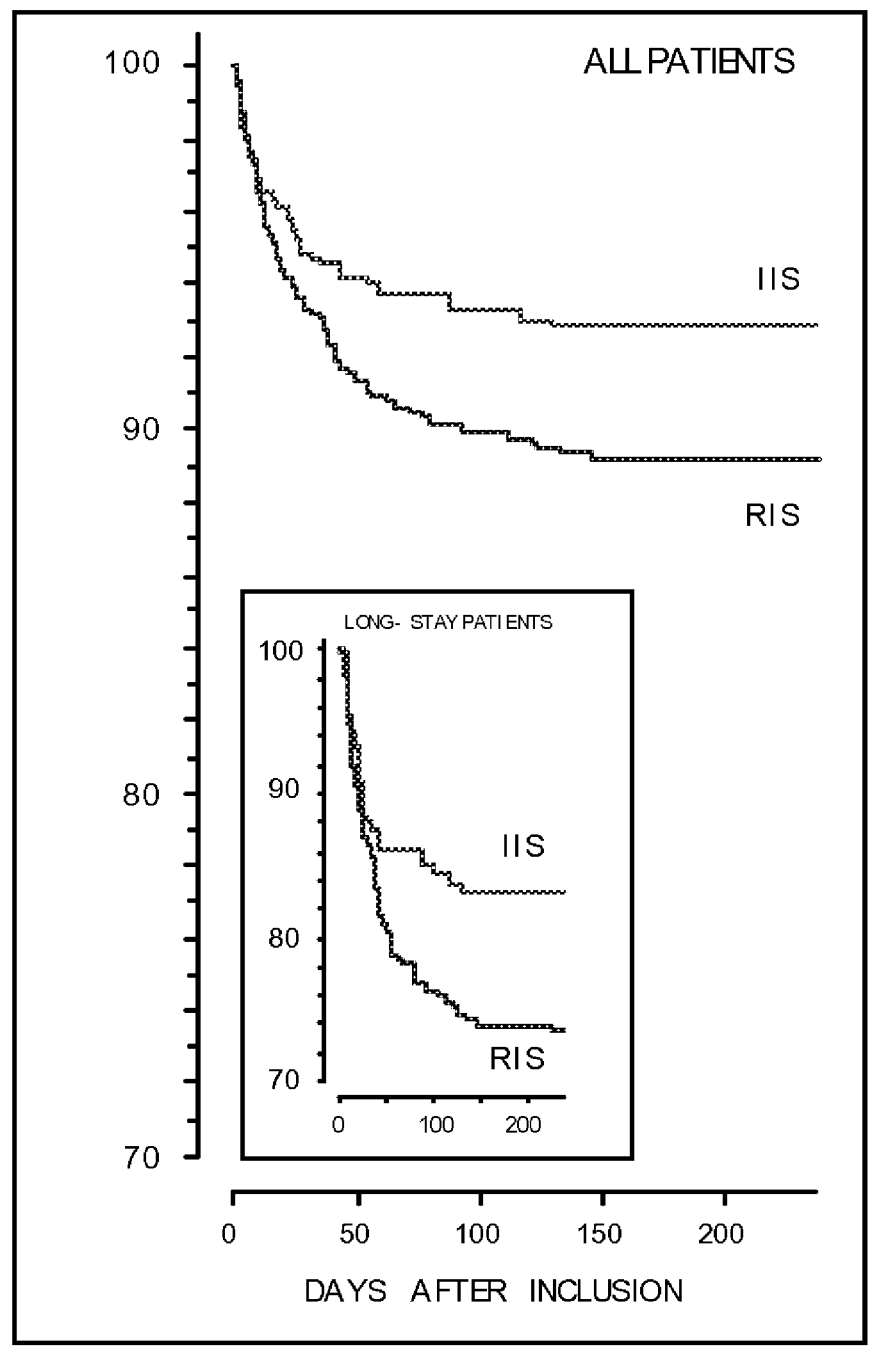
FIG. 2 shows Kaplan-Meier cumulative survival plot for in-hospital survival. The large figure displays results from all patients (P =0.01); the small figure displays long-stay (→5 days) ICU patients only (P =0.018). Bold lines represent the uS group and thin lines represent the RIS group. Patients discharged from the hospital were considered survivors. P-values were obtained by log rank (Mantel-Cox) significance testing.

Mortality Outcome (Tables 3 & 4; FIGS. 1 & 2)

In the IIS group, 35 patients (4.6%) died during intensive care versus 63 (8.1%) in the RIS group (P=0.005), a relative risk reduction (RRR) of 43% (Table 3). The "numbers needed to treat" (NNT) to save one life during intensive care was 29. The impact on ICU mortality by IIS was independent of the first 24 h-APACHE II and TISS scores (FIG. 1). The intervention effect was also similar in patients after cardiac surgery and those suffering from other types of critical illness. ICU mortality among the RIS patients actually receiving insulin was 12.4% versus 5.2% among those not requiring insulin to keep glycemia below 12 mmol/L (P=0.0003).

Since we hypothesized a difference in mortality among long-stay ICU patients, we sub-analysed the effect in patients with an ICU stay of $\leq 5$ days and in those staying >5 days. First 24 h-APACHE II score of patients staying $\leq 5$ days was a median 9 (IQR 6-12) and 75% of them were patients after cardiac surgery. Median first 24 h-APACHE II in patients staying >5 days was 12 (8-15) and 68% were suffering from a non-cardiac surgery type of critical illness. The number of patients with an ICU stay of >5 days was not statistically different in the IIS (27%) and RIS (31%) groups (P=0.1). Mortality of patients staying $\leq 5$ days was similar in IIS and RIS groups. Hence, the reduction in ICU mortality by IIS occurred selectively in the prolonged critically ill cohort with an absolute and relative risk reduction of 9.6% and 47%, respectively, and one life saved for every 11 treated long-stay patients.

All on-admission risk factors for ICU mortality were determined using univariate analysis. These comprised the first 24 h-APACHE II score, age, a non-cardiac surgery type of critical illness, tertiary referral, history of malignancy, and on-admission blood glucose level $\geq 11$ mmol/L. These factors were subsequently entered into a multivariate logistic regression model together with the randomized insulin schedule (Table 4). This revealed that the independent risk factors for mortality were the first 24 h-APACHE II score, age, a non-cardiac surgery type of critical illness, tertiary referral and insulin treatment schedule. The death odds ratio for IIS, corrected for other baseline univariate predictors of ICU death, was 0.52 (95% confidence intervals 0.33-0.82). Analysis of the causes of death during intensive care revealed that IIS particularly reduced the risk of death from multiple organ failure with a proven septic focus on post-mortem examination (Table 3).

IIS also significantly reduced total in-hospital mortality from 10.8% to 7.1% (P=0.01), a relative risk reduction of 34% (Table 3, FIG. 2). Again, this benefit was limited to the prolonged critically ill cohort.

Morbidity Outcome (Table 5)

IIS reduced duration of ICU stay whereas in-hospital stay was not detectably different between the two study groups. ICU re-admission rate was 2.1% and similar in both groups. In the IIS group, significantly less patients required prolonged mechanical ventilatory support and renal replacement therapy compared with the RIS group, whereas the need for inotropic or vasopressor support was identical. Independent of renal replacement therapy, kidney function parameters were more disturbed in the RIS group. The incidence of hyperbilirubinemia was significantly lower in the IIS group.

There was a 46% reduction in blood stream infections. Moreover, markers of inflammation were less disturbed and prolonged use of antibiotics (>10 days) less often required in the IIS group. The latter was largely attributable to the effect on bacteremia (75% of bacteremic patients were treated with antibiotics for >10 days versus 10% of non-bacteremic patients; P<0.0001). Mortality tended to be lower in bacteremic IIS patients (12.5%) compared with bacteremic RIS patients (29.5%; P=0.067). There was no difference between the two groups in the use of ICU drugs other than insulin or antibiotics.

Patients with an ICU stay of more than 1 week were screened weekly for critical illness polyneuropathy. Firstly, due to the effect on ICU stay, less IIS patients were screened. Secondly, among the screened patients in the IIS group, less revealed a positive EMG compared with the RIS group. Among screened patients, the NNT to prevent critical illness polyneuropathy in one patient was 4. Furthermore, critical illness polyneuropathy resolved more rapidly in the IIS group, as indicated by a lower fraction of patients with repetitive positive EMGs on the weekly screenings.

The use of aminoglycosides and glucocorticoids were determinants of critical illness polyneuropathy by univariate analysis. However, when entered into a multivariate logistic regression model together with other univariate predictors, the only independent determinants of critical illness polyneuropathy remained restrictive insulin schedule [or of 2.6 (1.6-4.2); P=0.0002], >3 days vasopressor treatment [or of 2.5 (1.4-4.2); P=0.001], acquiring a blood stream infection [or of 2.3 (1.3-4.1); P=0.006] and receiving renal replacement therapy [or of 1.9 (1.0-3.8); P=0.05].

When the risk of critical illness polyneuropathy was evaluated in both study groups as function of the actual mean glycemia per patient, a positive, linear correlation was obtained.

The amount of red cell transfusions in IIS patients was only half that of RIS patients. This was not due to a more liberal transfusion strategy in RIS patients as indicated by their lower levels of hemoglobin and hematocrit (Table 5).

The cumulative TISS score is an indicator of the number of therapeutic interventions per patient and per ICU stay (see Reis Miranda). There was a 20% reduction in median cumulative TISS score selectively in long-stay patients. In view of a comparable TISS score on the last day of study [median of 30 (26-38) in both study groups], this difference reflects a 20% reduction in costs per long-stay ICU patient (see Reis Miranda).

Discussion

In this large prospective, randomized, controlled study of intensive care-dependent critically ill patients, tight glycemic control below 6.1 mmol/L with insulin reduced ICU mortality by 43% and in-hospital mortality by 34%. Strict metabolic control also substantially improved morbidity by preventing blood stream infections, renal failure, anemia, critical illness polyneuropathy and need for prolonged support of failing vital organ systems. These striking benefits were independent of the type and severity of underlying disease.

The beneficial effects on morbidity can be summarized as reducing the risk of several key problems in intensive care. These include acquiring severe infections and ensuing inflammatory response, development of renal failure, cholestasis, anemia, critical illness polyneuropathy and muscle weakness. These problems perpetuate the need for intensive care which, in view of the high mortality of prolonged critical illness, often becomes futile.

In conclusion, the data suggest that disturbances in glucose metabolism in critically ill patients are not "adaptive and beneficial" since strict glycemic control during intensive care substantially reduces morbidity and mortality.

REFERENCES

Knaus: Knaus W A, Draper E A, Wagner D P, Zimmerman J E. APACHE II: A severity of disease classification system. Crit Care Med. 1985; 13:818-829.

Reis Miranda: Reis Miranda D, de Rijck A, Schaufeli W. Simplifed Therapeutic Intervention Scoring System: the TISS-28 items—results from a multicenter study. Crit Care Med. 1996; 24: 64-73.

Keene: Keene A R, Cukken D J. Therapeutic Intervention Scoring System: Update 1983. Crit Care Med. 1983; 11: 1-3.

Weinstein 1997: Weinstein M P, Towns M L, Quartey S M, Mirrett S, Reimer L G, Parmigiani G, Reller L B. The clinical significance of positive blood cultures in the 1990s: a prospective comprehensive evaluation of the microbiology, epidemiology and outcome of bacteremia and fungemia in adults. Clin Infect Dis. 1997; 24: 584-602.

Weinstein 1998: Weinstein M P, Mirrett S, Van Pelt L, McKinnon M, Zimmer B L, Kloos W, Reller L B. Clinical importance of identifying coagulase-negative staphylocci isolated from blood cultures: evaluation of microscan rapid and dried overnight gram-positive panels versus a conventional reference method. J Clin Microbiol. 1998; 36: 2089-2092.

TABLE 1

BASELINE PATIENT CHARACTERISTICS

|  | R I S | I I S | P-value |
|---|---|---|---|
| N | 783 | 765 |  |
| Male gender (% of patients) | 71 | 71 | 0.9 |
| Age (y) (mean ± SD) | 62.2 ± 13.9 | 63.4 ± 13.6 | 0.08 |
| BMI (kg/m^2) (mean ± SD) | 25.8 ± 4.7 | 26.2 ± 4.4 | 0.1 |
| Diagnostic group (total no.-%) |  |  |  |
| cardiac surgery | 493 (63%) | 477 (62%) | 0.8 |
| other types of critical illness | 290 (37%) | 288 (38%) |  |
| neurological disease, cerebral trauma or surgery | 30 (4%) | 33 (4%) |  |
| thoracic surgery and/or respiratory insufficiency | 56 (7%) | 66 (9%) |  |
| abdominal surgery/peritonitis | 58 (7%) | 45 (6%) |  |
| vascular surgery | 32 (4%) | 30 (4%) |  |
| multiple trauma or severe burns | 35 (4%) | 33 (4%) |  |
| transplantation | 44 (6%) | 46 (6%) |  |
| others | 35 (5%) | 35 (5%) |  |
| APACHE II score (median & IQR) |  |  |  |
| during the first 24 h | 9 (7-13) | 9 (7-13) | 0.4 |
| during the second 24 h | 9 (6-13) | 9 (6-13) | 0.8 |
| First 24 h APACHE II score □ 9 (total no.-%) | 458 (51%) | 429 (48%) | 0.3 |
| TISS score (median & IQR) |  |  |  |
| during the first 24 h | 43 (36-47) | 43 (37-46) | 0.7 |
| during the second 24 h | 38 (32-44) | 38 (31-43) | 0.4 |
| Tertiary referral (% of patients) | 17% | 17% | 0.7 |
| History of malignancy (% of patients) | 15% | 16% | 0.7 |
| History of diabetes (% of patients) | 13% | 13% | 0.9 |
| On admission blood glucose □ 6.1 mmol/L (% of patients) | 76% | 73% | 0.1 |
| On admission blood glucose □ 11 mmol/L (% of patients) | 12% | 11% | 0.2 |

APACHE denotes Acute Physiology and Chronic Health Evaluation. Higher APACHE II scores reflect more severe critical illness. First 24 h-APACHE II scores were artificially lowered by treatment effect and by assuming normal consciousness in sedated patients.
TISS denotes Therapeutic Intervention Scoring System, with each therapeutic intervention being assigned 1 to 4 points. An increasing score represents increasing intensity of treatment. The sum of points is calculated daily for each patient.
P-values were obtained using Student's t-test, Mann-Whitney-U test and Chi-square test, when appropriate.

TABLE 2

GLYCEMIA CONTROL

|  | R I S (N = 783) | I I S (N = 765) | P-value |
|---|---|---|---|
| Patients receiving insulin-total no. (%) | 307 (39%) | 755 (99%) | <0.0001 |
| Mean daily insulin dose, when given (IU/d) (median-IQR) | 33 (17-56) | 71 (48-100) | <0.0001 |
| Duration of insulin requirement (% of ICU stay) (median-IQR) | 67 (40-100) | 100 (100-100) | <0.0001 |
| Mean 06:00 h blood glucose level (mmol/L) (mean ± SD) | 8.5 ± 1.8 | 5.7 ± 1.0 | <0.0001 |
| Mean 06:00 h blood glucose level when on insulin (mmol/L) (mean ± SD) | 9.6 ± 1.8 | 5.7 ± 1.0 | <0.0001 |

P-values were obtained using Student's t-test, Mann-Whitney-U test and Chi-square test, when appropriate.

TABLE 3

MORTALITY ANALYSIS

| Outcome measure | R I S (N = 783) | I I S (N = 765) | RRR (%) | N N T | P-value |
|---|---|---|---|---|---|
| ICU deaths - total no. (%) | 63 (8.1%) | 35 (4.6%) | 43 | 29 | 0.005 |
| Death Odds Ratio corrected for other baseline risk factors (95% CI) |  | 0.52 (0.33-0.82) |  |  | 0.004 |
| ICU deaths in acute vs. prolonged critical illness |  |  |  |  |  |
| ICU deaths among patients staying ⩽5 days - total no. (%) | 14 (2.6%) | 13 (2.3%) | = |  | 0.8 |
| ICU deaths among patients staying >5 days - total no. (%) | 49 (20.2%) | 22 (10.6%) | 47 | 11 | 0.005 |
| ICU deaths per on-admission diagnostic group |  |  |  |  |  |
| Cardiac surgery - total no. (%) | 25 (5%) | 10 (2%) |  |  |  |
| Other types of critical illness - total no (%) | 38 (13.1%) | 25 (8.7%) |  |  |  |
| Neurological disease, cerebral trauma or surgery - total no. (%) | 7 (23.3%) | 6 (18.1%) |  |  |  |
| Thoracic surgery and/or respiratory insufficiency - total no. (%) | 10 (17.9%) | 5 (7.8%) |  |  |  |
| Abdominal surgery/peritonitis - total no (%) | 9 (15.5%) | 6 (13.3%) |  |  |  |
| Vascular surgery - total no. (%) | 2 (6.3%) | 2 (6.6%) |  |  |  |
| Multiple trauma or severe burns - total no. (%) | 3 (8.6%) | 4 (12.1%) |  |  |  |
| Transplantation - total no (%) | 1 (2.3%) | 2 (4.3%) |  |  |  |
| Others - total no (%) | 6 (17.1%) | 0 (0%) |  |  |  |
| Causes of death during intensive care -- total no |  |  |  |  | 0.02 |
| Multiple organ failure with proven septic focus | 33 | 8 |  |  |  |
| Multiple organ failure, no detectable septic focus | 18 | 14 |  |  |  |
| Severe brain damage | 5 | 3 |  |  |  |
| Cardiogenic shock | 7 | 10 |  |  |  |
| In-hospital deaths - total no. (%) | 85 (10.9%) | 55 (7.2%) | 34 | 27 | 0.01 |
| In-hospital deaths among patients staying ⩽5 days in ICU - total no. (%) | 21 (3.9%) | 20 (3.6%) | = |  | 0.8 |
| In-hospital deaths among patients staying >5 days in ICU - total no. (%) | 64 (26.3%) | 35 (16.8%) | 36 | 11 | 0.01 |

RRR denotes relative risk reduction. NNT denotes the number needed to treat to save one life. P-values were obtained using Chi-square test.

TABLE 4

Multivariate logistic regression analysis of
all baseline univariate predictors of ICU death

| Parameter | Odds Ratio | 95% Cl | P |
|---|---|---|---|
| Age (1 added y) | 1.03 | 1.01-1.05 | 0.002 |
| APACHE II during first 24 h ☐ 9 | 4.92 | 2.48-9.78 | <0.0001 |
| A non-cardiac surgery type of critical illness | 2.24 | 1.27-3.97 | 0.006 |
| Tertiary referral | 2.10 | 1.24-3.56 | 0.006 |
| A history of malignancy | 1.47 | 0.86-2.52 | 0.2 |
| Admission hyperglycemia | 1.66 | 0.96-2.87 | 0.07 |
| ☐ 11 mmol/L | | | |
| Intensive Insulin Treatment (IIS) | 0.52 | 0.33-0.82 | 0.004 |

APACHE denotes Acute Physiology and Chronic Health Evaluation. Higher APACHE II scores reflect more severe critical illness.

TABLE 5

MORBIDITY ANALYSIS

| Outcome measure | RIS (N = 783) | IIS (N = 765) | RRR (%) | NNT | P-value |
|---|---|---|---|---|---|
| ICU stay | | | | | |
| Days on ICU (median - IQR) | | | | | |
| ICU stay ≤5 days (N = 1097) | 2 (2-3) | 2 (2-3) | | | 0.2 |
| ICU stay >5 days (N = 451) | 15 (9-27) | 12 (8-20) | | | 0.003 |
| Patients requiring >7 days intensive care - total no (%) | 206 (26.3%) | 157 (20.5%) | 22 | 17 | 0.007 |
| Patients requiring >14 days intensive care - total no (%) | 123 (15.7%) | 87 (11.4%) | 27 | 23 | 0.01 |
| Patients requiring >21 days intensive care - total no (%) | 74 (9.5%) | 50 (6.5%) | 32 | 33 | 0.03 |
| Mechanical ventilatory support | | | | | |
| Days on mechanical ventilatory support (median - IQR) | | | | | |
| ICU stay ≤5 days (N = 1097) | 1 (1-2) | 1 (1-2) | | | 0.9 |
| ICU stay >5 days (N = 451) | 12 (7-23) | 10 (6-16) | | | 0.006 |
| Patients requiring >7 days ventilatory support - total no. (%) | 175 (23.2%) | 125 (16.9%) | 27 | 16 | 0.003 |
| Patients requiring >14 days ventilatory support - total no. (%) | 93 (12.3%) | 57 (7.7%) | 37 | 22 | 0.003 |
| Patients requiring >21 days ventilatory support - total no. (%) | 62 (8.2%) | 37 (5.0%) | 39 | 31 | 0.01 |
| Hemodynamics | | | | | |
| Patients on inotropic/vasopressor treatment - total no. (%) | 586 (75%) | 574 (75%) | = | | 0.9 |
| Renal function | | | | | |
| Peak plasma creatinine >2.5 mg/dL - total no. (%) | 96 (12.2%) | 69 (9.0%) | 26 | 31 | 0.04 |
| Peak plasma urea concentration >150 mg/dL - total no. (%) | 88 (11.2%) | 59 (7.7%) | 31 | 29 | 0.02 |
| Patients needing dialysis or CVVH - total no (%) | 64 (8.2%) | 37 (4.8%) | 42 | 29 | 0.007 |
| Liver function | | | | | |
| Patients with hyperbilirubinemia (peak bilirubin >2 mg/dL) - total no. (%) | 209 (27%) | 171 (22%) | 19 | 20 | 0.04 |
| Infection/Inflammation | | | | | |
| Patients with blood stream infections during intensive care - total no (%) | 61 (7.8%) | 32 (4.2%) | 46 | 28 | 0.00 |
| Patients treated with antibiotics for >10 days - total no. (%) | 134 (17.1%) | 86 (11.2%) | 35 | 17 | 0.0009 |
| >3 days C-reactive protein level above 150 mg/L - total no. (%) | 162 (21%) | 119 (15%) | 29 | 17 | 0.008 |
| >3 days white blood cell count ≤4000/µL or ☐12000/µL - total no. (%) | 166 (21%) | 121 (16%) | 24 | 20 | 0.006 |
| >3 days central body temperature ≤36° C. or ☐38° C. - total no. (%) | 206 (26%) | 164 (21%) | 19 | 20 | 0.02 |
| Critical illness polyneuropathy | | | | | |
| Patients with critical illness polyneuropathy - total no. (% of EMG-screened) | 110 (52%) | 47 (29%) | 44 | 4 | <0.0001 |
| Repetitive (>2) positive EMGs - total no (% of EMG screened) | 39 (19%) | 11 (7%) | 63 | 8 | 0.001 |
| Red cell transfusion requirement | | | | | |
| Number of patients requiring transfusion - total no (%) | 243 (31%) | 219 (29%) | | | 0.3 |
| Number of transfusions per patient (median - IQR) | 2 (1-3) | 1 (1-2) | | | 0.0002 |
| Lowest level of hemoglobin (g/dL) when transfused (median - IQR) | 8.1 (7.6- 8.6) | 8.3 (7.7-8.9) | | | 0.02 |
| Lowest level of hematocrit (%) when transfused (median - IQR) | 0.25 (0.24-0.27) | 0.26 (0.24- 0.27) | | | 0.03 |
| Cumulative TISS (median - IQR) | | | | | |
| ICU stay ≤5 days (N = 1097) | 84 (67-111) | 85 (68-115) | | | 0.3 |
| ICU stay >5 days (N = 451) | 536 (329-956) | 431 (271-670) | | | 0.0008 |

RRR denotes relative risk reduction. NNT denotes the number needed to treat to prevent one patient from acquiring the studied complication. EMG denotes electromyography and CVVH continuous veno-venous hemofiltration. P-values were obtained using Mann-Whitney-U test and Chi-square test, when appropriate. The analysis of number of transfusions did not take the admission day into account.

What is claim is:

1. A method of treating a critically ill patient or a critically ill polyneuropathy (CIPNP) patient having a blood glucose level of greater than 130 mg/dL, said method comprising administering to said critically ill patient or CIPNP patient a blood glucose regulator selected from the group consisting of insulin, an insulin analogue, an active derivative of insulin or an insulin analogue, and a physiologically acceptable salt of said derivative in an amount effective to reduce blood glucose levels in said patient to within a range of from about 60 mg/dL to about 130 mg/dL, wherein said blood glucose regulator is administered intravenously and continuously infused to said patient as needed for at least 24 hours and the blood glucose level is maintained within a range of from about 60 mg/dL to about 130 mg/dL for 24 hours or more and wherein said treatment reduces the incidence of mortality in critically ill patients or CIPNP patients.

2. The method of claim 1 wherein the critically ill patient or CIPNP patient is a patient who has been diagnosed as having diabetes.

3. The method of claim 2, wherein the blood glucose regulator administered to said patient is $Asp^{B28}$ human insulin.

4. A method of treating a critically ill patient or a critically ill polyneuropathy (CIPNP) patient having a blood glucose level of greater than 130 mg/dL, said method comprising administering to said critically ill patient or CIPNP patient a blood glucose regulator selected from the group consisting of insulin, an insulin analogue, an active derivative of insulin or an insulin analogue, and a physiologically acceptable salt of said derivative in an amount effective to reduce blood glucose levels in said patient to within a range of from about 60 mg/dL to about 130 mg/dL, wherein said blood glucose regulator is administered intravenously and continuously infused to said patient as needed for at least 24 hours and the blood glucose level is maintained within a range of from about 60 mg/dL to about 130 mg/dL for 24 hours or more and wherein said treatment reduces the incidence of critical illness polyneuropathy in critically ill patients or CIPNP patients.

5. The method of claim 4 wherein the critically ill patient or CIPNP patient is a patient who has been diagnosed as having diabetes.

6. The method of claim 5, wherein the blood glucose regulator administered to said patient is $Asp^{B28}$ human insulin.

7. A method of treating a critically ill patient or a critically ill polyneuropathy (CIPNP) patient having a blood glucose level of greater than 130 mg/dL, said method comprising administering to said critically ill patient or CIPNP patient a blood glucose regulator selected from the group consisting of insulin, an insulin analogue, an active derivative of insulin or an insulin analogue, and a physiologically acceptable salt of said derivative in an amount effective to reduce blood glucose levels in said patient to within a range of from about 60 mg/dL to about 130 mg/dL, wherein said blood glucose regulator is administered intravenously and continuously infused to said patient as needed for at least 24 hours and the blood glucose level is maintained within a range of from about 60 mg/dL to about 130 mg/dL for 24 hours or more and wherein said treatment reduces the incidence of sepsis in critically ill patients or CIPNP patients.

8. The method of claim 7 wherein the critically ill patient or CIPNP patient is a patient who has been diagnosed as having diabetes.

9. The method of claim 8, wherein the blood glucose regulator administered to said patient is $Asp^{B28}$ human insulin.

10. A method of treating a critically ill patient or a critically ill polyneuropathy (CIPNP) patient having a blood glucose level of greater than 130 mg/dL, said method comprising administeringto said critically ill patient or CIPNP patient a blood glucose regulator selected from the group consisting of insulin, an insulin analogue, an active derivative of insulin or an insulin analogue, and a physiologically acceptable salt of said derivative in an amount effective to reduce blood glucose levels in said patient to within a range of from about 60 mg/dL to about 130 mg/dL, wherein said blood glucose regulator is administered intravenously and continuously infused to said patient as needed for at least 24 hours and the blood glucose level is maintained within a range of from about 60 mg/dL to about 130 mg/dL for 24 hours or more and wherein said treatment reduces the incidence of renal failure in critically ill patients or CIPNP patients.

11. The method of claim 10 wherein the critically ill patient or CIPNP patient is a patient who has been diagnosed as having diabetes.

12. The method of claim 11, wherein the blood glucose regulator administered to said patient is $Asp^{B28}$ human insulin.

13. A method of treating a critically ill patient or a critically ill polyneuropathy (CIPNP) patient having a blood glucose level of greater than 130 mg/dL, said method comprising administering to said critically ill patient or CIPNP patient a blood glucose regulator selected from the group consisting of insulin, an insulin analogue, an active derivative of insulin or an insulin analogue, and a physiologically acceptable salt of said derivative in an amount effective to reduce blood glucose levels in said patient to within a range of from about 60 mg/dL to about 130 mg/dL, wherein said blood glucose regulator is administered intravenously and continuously infused to said patient as needed for at least 24 hours and the blood glucose level is maintained within a range of from about 60 mg/dL to about 130 mg/dL for 24 hours or more and wherein said treatment reduces the incidence of multiple organ failure in critically ill patients or CIPNP patients.

14. The method of claim 13 wherein the critically ill patient or CIPNP patient is a patient who has been diagnosed as having diabetes.

15. The method of claim 14, wherein the blood glucose regulator administered to said patient is $Asp^{B28}$ human insulin.

* * * * *